(12) United States Patent
Hargro

(10) Patent No.: US 6,398,953 B1
(45) Date of Patent: Jun. 4, 2002

(54) CHROMATOGRAPHY CARTRIDGE END CAP FIXATION

(75) Inventor: Ivan Hargro, Charlottesville, VA (US)

(73) Assignee: Dyax Corporation, Cambridge, OH (US)

( * ) Notice: Subject to any disclaimer, the term of this patent is extended or adjusted under 35 U.S.C. 154(b) by 0 days.

(21) Appl. No.: 09/586,847

(22) Filed: Jun. 5, 2000

Related U.S. Application Data

(62) Division of application No. 09/276,589, filed on Mar. 25, 1999, now Pat. No. 6,117,329.

(51) Int. Cl.$^7$ .............................................. B01D 15/08
(52) U.S. Cl. .................................. 210/198.2; 210/656
(58) Field of Search ............................... 210/635, 656, 210/659, 198.2, 232, 238, 282; 96/101, 106; 29/447

(56) References Cited

U.S. PATENT DOCUMENTS

| | | | |
|---|---|---|---|
| 1,101,084 A | 6/1914 | McCarty ....................... 29/447 |
| 1,736,610 A | 11/1929 | Loffler .......................... 29/447 |
| 2,401,231 A | 5/1946 | Crawford ...................... 220/64 |
| 2,647,847 A | 8/1953 | Black et al. .................... 148/4 |
| 3,511,377 A | 5/1970 | Hrdina ........................ 210/198 |
| 3,574,252 A | 4/1971 | Rackoff et al. ............. 29/148.4 |
| 3,731,367 A | 5/1973 | Laussermair et al. ......... 29/447 |
| 3,900,939 A | 8/1975 | Greacen ....................... 29/401 |
| 3,966,609 A | 6/1976 | Godbille et al. ........ 210/198 C |
| 4,167,351 A | 9/1979 | Bindin ......................... 403/30 |
| 4,198,081 A | 4/1980 | Harrison et al. ............. 285/381 |
| 4,280,905 A | 7/1981 | Gunkel et al. ........... 210/198.2 |
| 4,293,942 A | 10/1981 | Baumgartner ............... 368/280 |
| 4,314,396 A | 2/1982 | Nunlist et al. ......... 29/156.8 R |
| 4,332,073 A | 6/1982 | Yoshida et al. ........... 29/421 R |
| 4,333,223 A | 6/1982 | Germann ..................... 29/447 |
| 4,377,335 A | 3/1983 | Fannon et al. ............. 355/3 FU |
| 4,377,894 A | 3/1983 | Yoshida ..................... 29/421 R |
| 4,451,365 A | 5/1984 | Sattler et al. ............. 210/198.2 |
| 4,565,632 A | 1/1986 | Hatch et al. ................. 210/656 |
| 4,636,316 A | 1/1987 | Harris et al. ................. 210/656 |
| 4,670,141 A | 6/1987 | Shackelford et al. ..... 210/198.2 |
| 4,732,687 A | 3/1988 | Muller et al. ............... 210/656 |
| 4,891,133 A | 1/1990 | Colvin, Jr. ................ 210/198.2 |
| 4,968,421 A | 11/1990 | Spacek et al. ............ 210/198.2 |
| 4,976,307 A | 12/1990 | Hall et al. ..................... 165/76 |
| 5,021,162 A | 6/1991 | Sakamoto et al. ........... 210/635 |
| 5,137,628 A | 8/1992 | Hart et al. ................ 210/198.2 |
| 5,167,810 A | 12/1992 | Vassarotti et al. ........ 210/198.2 |
| 5,199,171 A | 4/1993 | Umezawa et al. ........ 29/898.07 |
| 5,238,556 A | 8/1993 | Shirkhan .................. 210/198.2 |
| 5,378,361 A | 1/1995 | Baeckstrum ............. 210/198.2 |
| 5,601,708 A | 2/1997 | Leavesley ................. 210/198.2 |
| 5,671,928 A | 9/1997 | Lanyi et al. ............. 277/207 R |
| 5,767,444 A | 6/1998 | Heimlicher ............... 175/50.61 |
| 6,001,253 A | 12/1999 | Conroy ........................ 210/635 |
| 6,019,897 A | 2/2000 | Horsman .................. 210/198.2 |
| 6,074,556 A | * | 6/2000 | Van Davelaar .......... 210/198.2 |

* cited by examiner

Primary Examiner—Ernest G. Therkorn
(74) Attorney, Agent, or Firm—Fish & Richardson P.C.

(57) ABSTRACT

A method of forming a chromatography cartridge includes providing a flexible-walled tube, placing a first end cap within the tube in sealing engagement with the tube wall, forming a media bed within the tube supported by the first end cap, cooling a second end cap to thermally contract the second end cap, placing the contracted second end cap within the tube and against the media bed, and sealing the second end cap to the tube wall by thermal expansion of the second end cap upon warming. The expansion of the second end cap causes the tube wall to deform. A chromatography column includes a flexible-walled tube containing chromatography media, and an end cap positioned within the tube. The end cap has a dimension greater than an inner dimension of the tube such that the tube is locally deformed by the end cap.

13 Claims, 2 Drawing Sheets

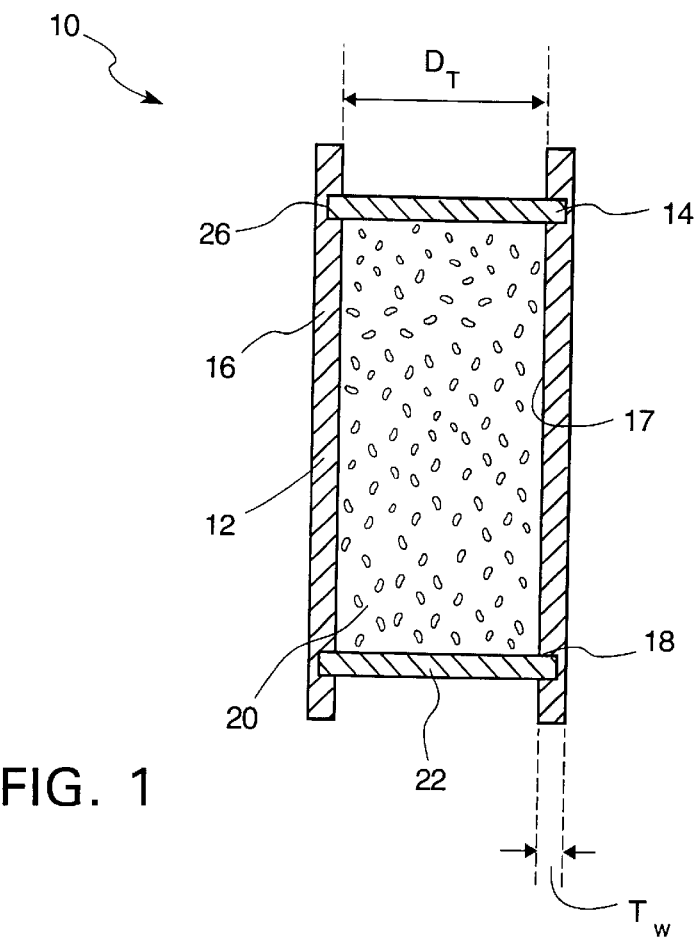
FIG. 1
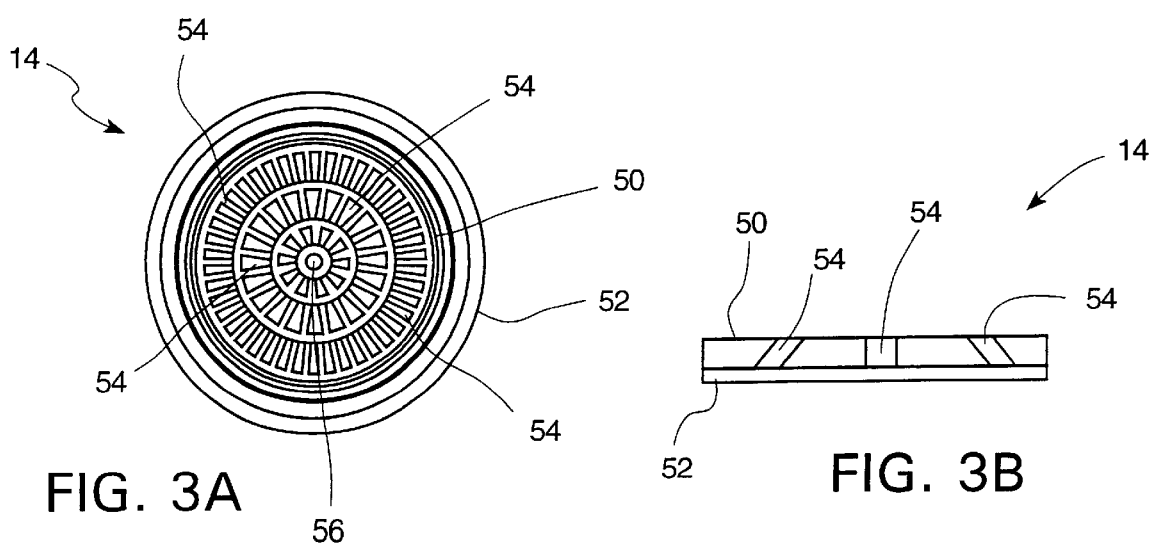
FIG. 3A
FIG. 3B

CHROMATOGRAPHY CARTRIDGE END CAP FIXATION

This application is a divisional (and claims the benefit of priority under 35 USC 120) of U.S. application Ser. No. 09/276,589, filed Mar. 25, 1999, now U.S. Pat. No. 6,117,329.

BACKGROUND OF THE INVENTION

The invention relates to method and apparatus for securing an end cap within a chromatography cartridge.

Liquid column chromatography is a technique for identifying, separating, or purifying individual components in a subject sample. In employing the technique, a "stationary phase," such as a surface active powder, is packed into a chromatography column to form a chromatography media bed. A "mobile phase" consisting of a carrier liquid and a sample to be identified, analyzed, or purified is passed through the column. Different compounds in the sample migrate through the column at different rates, depending, e.g., on their size and degree of attraction to the stationary phase in the column. Consequently, the different compounds in the liquid emerge from the column at different times, allowing separation of the compounds in the sample. For a description of column chromatography, see McDonald et al., U.S. Pat. No. 4,250,035, entitled "Radial Compression of Packed Beds," incorporated herein by reference.

Liquid column chromatography can be carried out using a disposable cylindrical cartridge. The cartridge contains the media bed bounded axially at both ends by an end cap. The end caps are secured firmly within the cartridge to axially support the media bed. Known methods of securing the end caps include threading and the use of pre-formed retention grooves.

SUMMARY OF THE INVENTION

In general, in one aspect, the invention features a method of forming a chromatography cartridge including providing a flexible-walled tube, placing a first end cap within the tube in sealing engagement with a wall of the tube, forming a media bed within the tube supported by the first end cap, cooling a second end cap to thermally contract the second end cap to a dimension less than an inner dimension of the tube, placing the second end cap within the tube and against the media bed, and sealing the second end cap to the tube wall by thermal expansion of the second end cap upon warming. The expansion of the second end cap causes the tube wall to deform.

Embodiments of this aspect of the invention may include one or more of the following features. The first end cap is cooled prior to placing the first end cap within the tube and the first end cap is sealed to the tube wall by thermal expansion of the first end cap upon warming. The expansion of the first end cap causes the tube wall to deform.

The tube wall has an inner surface which defines a section of constant inner diameter for slidably receiving the second end cap.

According to another aspect of the invention, a method of supporting a media bed in a chromatography cartridge tube includes cooling an end cap to thermally contract the end cap to a dimension less than an inner dimension of the tube, placing the contracted end cap within the tube and against the media bed, and sealing the end cap to the tube by thermal expansion of the end cap upon warming. The expansion of the end cap causes the tube to deform.

Embodiments of this aspect of the invention may include one or more of the following features.

The end cap is cooled with liquid nitrogen.

In an illustrated embodiment, the tube and the end cap are cylindrical and cooling the end cap thermally contracts the end cap to a diameter less than an inner diameter of the tube. Expansion of the end cap causes, e.g., about a 1 to 10 percent, preferably about a 2 percent, increase in the inner diameter of the tube. The end cap has, at room temperature, a diameter of, e.g., about 1 to 10 percent, preferably about 2 to 4 percent, larger than the inner diameter of the tube. The cooling step contracts the end cap to a diameter of, e.g., about 0.1 to 1 percent less than the inner diameter of the tube.

The tube is formed from a polymeric material, and the end cap is formed from a polymeric material or a metal. Alternatively, the tube and the end cap are both metal.

The end cap includes a flow distributor and a sieve.

According to another aspect of the invention, a chromatography column assembly includes a flexible-walled tube for containing chromatography media, and an end cap for positioning within the tube. The end cap, at a first temperature, has a first dimension greater than an inner dimension of the tube. The end cap is configured such that upon cooling to a second temperature lower than the first temperature, the end cap thermally contracts to a second dimension less than the inner dimension of the tube permitting placement of the end cap within the tube. Upon warming, the end cap expands to deform the tube to seal the end cap against the tube.

According to another aspect of the invention, a chromatography column includes a flexible-walled tube containing chromatography media, and an end cap positioned within the tube. The end cap has a dimension greater than an inner dimension of the tube such that the tube is locally deformed by the end cap in a region in which the end cap is positioned to secure the end cap within the tube. The end cap is configured to thermally contract upon cooling to a dimension less than the inner dimension of the tube to permit placement of the end cap within the tube.

Embodiments of the invention may include one or more of the following advantages. The end cap can be fixed at any height within the cartridge as dictated by the height of the media bed. The intimate seal between the end cap and wall of the tube limits build-up of debris between the end cap and tube wall.

BRIEF DESCRIPTION OF THE DRAWINGS

FIG. 1 is a cross-sectional view of a column chromatography cartridge of the invention.

FIG. 3A is a plan view of an end cap of the column chromatography cartridge of FIG. 1.

FIG. 3B is an end view of the end cap of FIG. 3A.

DESCRIPTION OF THE PREFERRED EMBODIMENT

Figure 2:
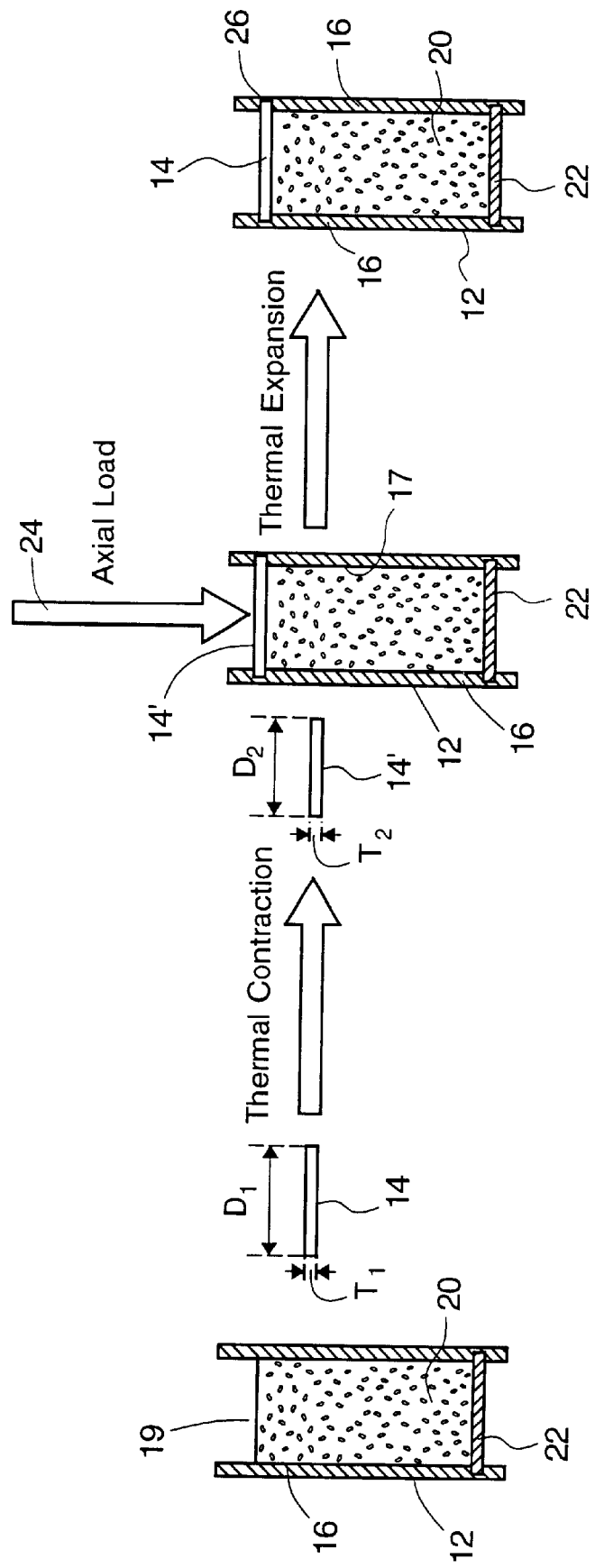
FIG. 2 is a schematic illustration of the process of forming the column chromatography cartridge of FIG. 1.

Referring to FIG. 1, a column chromatography cartridge 10 includes a flexible-walled, cylindrical tube 12 and top and bottom cylindrical end caps 14, 22. Located within tube 12 and supported between end caps 14, 22 is a chromatography media bed 20. Bottom end cap 22 is fixed in place using any conventionally known technique, e.g., a retention groove or threaded component. After forming media bed 20 within tube 12, top end cap 14 is placed within tube 12 against media bed 20 and secured in place.

Since the height of media bed 20 can vary, the position of top end cap 14 can also vary. To permit variable positioning of top end cap 14, top end cap 14 is formed of a material which thermally contracts upon cooling. When cooled, e.g., with liquid nitrogen, the diameter of top end cap 14 is smaller than the inner diameter of tube 12, permitting top end cap 14 to be placed within tube 12. Wall 16 has a smooth inner surface 17 allowing top end cap 14 to be slid within tube 12 to any desired height. Once positioned inside tube 12, top end cap 14 expands to its original dimensions upon warming to the ambient temperature, e.g., room temperature.

At ambient temperature, the diameter of top end cap 14 is larger than the inner diameter of tube 12. Because wall 16 of tube 12 is flexible, the expansion of top end cap 14 while positioned within tube 12 acts to locally deform tube 12 in a region 26 of the tube, sealing top end cap 14 against inner surface 17 of wall 16. Top end cap 14 is sealed against wall 16 in region 26 by a mechanical and frictional interference fit.

Referring to FIG. 2, to fix top end cap 14 within tube 12, top end cap 14 is cooled and then, in its contracted state (shown as end cap 14'), inserted into an open end 19 of tube 12 and pushed against bed 20 by an axial load 24. The top end cap is held against bed 20 by axial load 24 until the end cap warms to the ambient temperature. As the top end cap warms, it thermally expands from its contracted diameter to its ambient temperature diameter. Cartridge 10 is then ready to be used in column chromatography separation procedures, as described, e.g., in Van Davelaar, U.S. patent application Ser. No. 09/264,846, entitled "Cartridge Sealing Apparatus and Method," now U.S. Pat. No. 6,074,556, filed Mar. 2, 1999, and Green et al., abandoned U.S. patent application Ser. No. 08/970,287, entitled "Liquid Chromatography Column," filed Nov. 14, 1997, both incorporated herein by reference.

Top end cap 14 has, at room temperature, a diameter of, e.g., about 1 to 10 percent, preferably about 2 to 4 percent larger than the inner diameter of the tube. For example, for a tube 12 having an inner diameter, $D_T$, of about 3.110 inches, and a wall thickness $T_w$ of, e.g., about 0.25 inches, top end cap 14 has, at room temperature, a diameter, $D_1$, of about 3.170 inches, and a thickness, T1, of, e.g., about 0.25 inches. When cooled, e.g., to −196° C. with liquid nitrogen, top end cap 14' has a diameter, $D_2$, of, e.g., about 0.1 to 1 percent smaller than diameter $D_T$, preferably about 3.100 inches, and a thickness $T_2$, of, e.g., about 0.245 inches. Thermal expansion of top end cap 14 from diameter $D_2$ to diameter $D_1$ deforms flexible wall 16 of tube 12 by, e.g., about 1 to 10 percent, preferably about 0.030 inches (about 2 percent), creating a 0.030 inch interference fit.

Referring to FIGS. 3A and 3B, top end cap 14 includes an upper flow distribution portion 50 and a lower frit portion 52. The flow distribution portion 50 includes a plurality of apertures 54 for distributing incoming mobile phase fluid. Frit portion 52 is constructed from a porous material and acts as a sieve permitting mobile phase fluid to pass through to media bed 20 while preventing the media in bed 20 from passing therethrough.

Tube 12 and plate 14 are both made from, e.g., polyethylene. Both tube 12 and end cap 14 can be made from, e.g., other polymers, such as polypropylene and PEEK™, or from sintered metals, such as stainless steel or titanium. In addition, tube 12 and end cap 14 can be made from different materials, as long as the material forming end cap 14 is at least as strong as the material forming wall 16 of tube 12. For example, end cap 14 can be a metal when tube 12 is a polymer or a metal.

If the material forming end cap 14 is stronger than the material forming tube 12 (e.g., end cap 14 is metal and tube 12 is polyethylene), then the profile of the interference fit in region 26 will resemble the profile of end cap 14. That is, end cap 14 will deform tube 12, but tube 12 will not deform end cap 14. If, however, end cap 12 and tube 14 are formed from materials of similar strength (e.g., both polyethylene), then end cap 14 and tube 12 will both deform as end cap 14 expands within tube 12, creating a curved, molded interference fit within region 26.

Other embodiments are within the scope of the following claims.

For example, in addition to or alternative to cooling end cap 14, tube 12 might be heated to expand the diameter of end cap 14 before inserting end cap 14 within tube 12.

End cap 14 and tube 12 can have shapes and dimensions other than those described above, as long as the difference between the thermally contracted and ambient temperature dimensions of the end cap in combination with the flexibility of the tube wall permit the end cap to be positioned within the tube when contracted, and to deform the tube wall upon return of the end cap to its ambient temperature dimensions.

Distribution portion 50 and frit portion 52 can be joined, e.g., by sintering, or can be separate components.

The ambient temperature can be, e.g., room temperature, or a different controlled temperature.

End cap 14 need not be thermally contracted using liquid nitrogen. Depending on the amount of contraction required, end cap 14 can be cooled to temperatures greater or less than −196° C.

The cryogenic fixation method described above with reference to FIG. 2 can be used to seal bottom end cap 22 within tube 12.

The above described cryogenic fixation procedure need not be limited to column chromatography cartridges. The procedure described can be used to affix any form of end cap at variable height within a walled flow through cartridge.

What is claimed is:

1. A chromatography column assembly comprising:
    a flexible-walled tube for containing chromatography media, and
    an end cap for positioning within the tube, the end cap, at a first temperature, having a first dimension greater than an inner dimension of the tube, the end cap being configured such that upon cooling to a second temperature lower than the first temperature, the end cap thermally contracts to a second dimension less than the inner dimension of the tube permitting placement of the end cap within the tube, and, upon warming, the end cap expands to deform the tube to seal the end cap against the tube.

2. The assembly of claim 1 wherein the tube and the end cap are cylindrical.

3. The assembly of claim 1 wherein the end cap, at the first temperature, has a diameter of about 2 to 4 percent larger than an inner diameter of the tube.

4. The assembly of claim 2 wherein the end cap, upon cooling to the second temperature, has a diameter of about 0.1 to 1 percent less than an inner diameter of the tube.

5. The assembly of claim 1 wherein the tube comprises a polymeric material.

6. The assembly of claim 5 herein the end cap comprises a material selected from the group consisting of a polymer and a metal.

7. The assembly of claim 1 wherein the tube comprises a metal material.

8. The assembly of claim 7 wherein the end cap comprises a metal material.

9. The assembly of claim 1 wherein an inner surface of the flexible-walled tube defines a section of constant inner diameter for slidably receiving the end cap prior to expansion of the end cap.

10. The assembly of claim 1 wherein the end cap comprises a flow distributor.

11. The assembly of claim 1 wherein the end cap comprises a sieve.

12. The assembly of claim 1 further comprising a second end cap for positioning within the tube, the second end cap, at the first temperature, having a first dimension greater than an inner dimension of the tube, the second end cap being configured such that upon cooling to the second temperature, the second end cap thermally contracts to the second dimension less than the inner dimension of the tube permitting placement of the second end cap within the tube, and upon warming the second end cap expands to deform the tube to seal the second end cap against the tube.

13. A chromatography column, comprising:
   a flexible-walled tube containing chromatography media, and
   an end cap positioned within the tube, the end cap having a dimension greater than an inner dimension of the tube such that the tube is locally deformed by the end cap in a region in which the end cap is positioned to secure the end cap within the tube, the end cap being configured to thermally contract upon cooling to a dimension less than the inner dimension of the tube to permit placement of the end cap within the tube.

* * * * *